(12) United States Patent
Caruso et al.

(10) Patent No.: US 12,726,826 B2
(45) **Date of Patent: *Sep. 1, 2026**

(54) AUTHORIZING PROGRAMMING OF AN IMPLANTED DEVICE USING SECOND FACTOR

(71) Applicant: Verily Health Inc., Dallas, TX (US)

(72) Inventors: Michael Andrew Caruso, Castro Valley, CA (US); Adam Bildersee, Burlingame, CA (US); Nehal Patel, Burlingame, CA (US); James Salvia, Belmont, CA (US); Arvind Govindaraj, San Bruno, CA (US)

(73) Assignee: Verily Health Inc., Dallas, TX (US)

( * ) Notice: Subject to any disclaimer, the term of this patent is extended or adjusted under 35 U.S.C. 154(b) by 14 days.

This patent is subject to a terminal disclaimer.

(21) Appl. No.: 18/588,430

(22) Filed: Feb. 27, 2024

(65) Prior Publication Data

US 2024/0205685 A1 Jun. 20, 2024

Related U.S. Application Data

(63) Continuation of application No. 15/930,580, filed on May 13, 2020, now Pat. No. 11,924,645.

(Continued)

(51) Int. Cl.

*G06F 15/16* (2006.01)
*A61N 1/372* (2006.01)

(Continued)

(52) U.S. Cl.

CPC ........ *H04W 12/50* (2021.01); *A61N 1/37223* (2013.01); *A61N 1/37229* (2013.01);

(Continued)

(58) Field of Classification Search

CPC ... H04W 12/50; H04W 76/14; H04W 12/037; A61N 1/37254; A61N 1/37223;

(Continued)

(56) References Cited

U.S. PATENT DOCUMENTS

| | | |
|---|---|---|
| 4,561,443 A | 12/1985 | Hogrefe et al. |
| 7,155,290 B2 | 12/2006 | Von Arx et al. |

(Continued)

FOREIGN PATENT DOCUMENTS

| | | |
|---|---|---|
| WO | 2018156386 | 8/2018 |

OTHER PUBLICATIONS

"Bluetooth SIG Proprietary Bluetooth Core Specification v5.0", Available Online at: https: //www.bluetooth.org/en-us/specification/adopted-specifications, Dec. 6, 2016, pp. 1-2822.

(Continued)

*Primary Examiner* — Normin Abedin
(74) *Attorney, Agent, or Firm* — Kilpatrick Townsend & Stockton LLP

(57) ABSTRACT

Described herein are techniques to ensure a user using an external device is authorized to connect and connecting to a correct implantable medical device using a wireless communication protocol. A request for authorization is sent to the external device from the implantable medical device, and the authorization can be provided by an authorization pulse sent using the implantable medical device charger over the inductive link between the charging device and the implanted device. The authorization pulse can be trusted because the inductive link is short range, ensuring the patient is aware of the connection to the implanted device. Once the implanted device receives the authorization pulse, it may finalize the pairing over the first connection.

20 Claims, 4 Drawing Sheets

Related U.S. Application Data

(60) Provisional application No. 62/847,359, filed on May 14, 2019.

(51) Int. Cl.

| | |
|---|---|
| ***A61N 1/378*** | (2006.01) |
| ***G16H 40/67*** | (2018.01) |
| ***H04W 12/037*** | (2021.01) |
| ***H04W 12/50*** | (2021.01) |
| ***H04W 76/14*** | (2018.01) |

(52) U.S. Cl.
CPC ..... *A61N 1/37247* (2013.01); *A61N 1/37254* (2017.08); *A61N 1/3787* (2013.01); *G16H 40/67* (2018.01); *H04W 12/037* (2021.01); *H04W 76/14* (2018.02)

(58) Field of Classification Search
CPC ............ A61N 1/37229; A61N 1/37247; A61N 1/3787; G16H 40/67
See application file for complete search history.

(56) References Cited

U.S. PATENT DOCUMENTS

| | | | | |
|---|---|---|---|---|
| 7,228,182 | B2 | 6/2007 | Healy et al. | |
| 7,406,349 | B2 | 7/2008 | Seeberger et al. | |
| 7,831,828 | B2 | 11/2010 | Von Arx et al. | |
| 9,106,203 | B2 | 8/2015 | Kesler et al. | |
| 9,991,753 | B2 | 6/2018 | Miller et al. | |
| 10,187,792 | B2 * | 1/2019 | Meskens | A61N 1/36038 |
| 10,305,692 | B2 | 5/2019 | Peterson | |
| 10,327,706 | B2 | 6/2019 | Yarger et al. | |
| 2005/0204134 | A1 | 9/2005 | Von Arx et al. | |
| 2008/0058900 | A1 * | 3/2008 | Berthelsdorf | A61N 1/37254 607/59 |
| 2008/0132982 | A1 | 6/2008 | Gerber | |
| 2009/0182388 | A1 | 7/2009 | Von Arx et al. | |
| 2010/0010587 | A1 | 1/2010 | Skelton et al. | |
| 2013/0006332 | A1 | 1/2013 | Sommer et al. | |
| 2014/0273824 | A1 | 9/2014 | Fenner et al. | |
| 2014/0357187 | A1 | 12/2014 | Ehrensvard | |
| 2015/0065047 | A1 | 3/2015 | Wu et al. | |
| 2015/0089590 | A1 | 3/2015 | Krishnan et al. | |
| 2015/0300923 | A1 | 10/2015 | Halbert | |
| 2016/0156528 | A1 | 6/2016 | Aloush | |
| 2017/0118543 | A1 | 4/2017 | Ha et al. | |
| 2017/0259072 | A1 * | 9/2017 | Newham | A61N 1/37276 |
| 2018/0078777 | A1 * | 3/2018 | Wu | A61N 1/37252 |
| 2018/0241564 | A1 | 8/2018 | Peterson | |
| 2018/0243573 | A1 | 8/2018 | Yoder et al. | |
| 2020/0094062 | A1 * | 3/2020 | Yoder | H04W 12/069 |

OTHER PUBLICATIONS

U.S. Appl. No. 15/930,580 , "Final Office Action", Apr. 5, 2023, 10 pages.

U.S. Appl. No. 15/930,580 , "Non-Final Office Action", Sep. 19, 2022, 9 pages.

U.S. Appl. No. 15/930,580 , "Notice of Allowance", Oct. 26, 2023, 8 pages.

Adeeb et al., "An Inductive Link-Based Wireless Power Transfer System for Biomedical Applications", Active and Passive Electronic Components, vol. 2012, May 2012, 11 pages.

Ali et al., "Inductive link design for medical implants", 2009 IEEE Symposium on Industrial Electronics and Applications, ISIEA 2009—Proceedings, vol. 2, Oct. 4-6, 2009, 6 pages.

Bose , "Pairing a Bluetooth® Device with NFC", https://www.bose.com/en_us/support/article/pairing-a-bluetooth-enabled-device-with-nfc-qc35.html, Accessed from Internet on: Aug. 26, 2020,.

Brusamarello et al., "Power Transfer With an Inductive Link and Wireless Tuning", IEEE Transactions on Instrumentation and Measurement, vol. 62, May 5, 2013, pp. 924-931.

Chi et al., "e-SAFE: Secure, Efficient and Forensics-enabled Access to Implantable Medical Devices", IEEE Conference on Communications and Network Security (CNS), Apr. 6, 2018, 9 pages.

EP20806059.0 , "Extended European Search Report", Dec. 20, 2022, 12 pages.

Hei et al., "Poster: Near Field Communication Based Access Control for Wireless Medical Devices", Proceedings of the 15th ACM International Symposium on MobiHoc Networking and Computing, Aug. 11-14, 2014, 2 pages.

Maffei , "Tags for Multi-Protocol Authentication", Electronic Notes in Theoretical Computer Science, vol. 128, No. 5, May 3, 2005, pp. 55-63.

PCT/US2020/032925 , "International Search Report and Written Opinion", Jul. 27, 2020, 14 pages.

Sawan et al., "Power and Data Managements: Inductive Links", GMB8320 Dispositifs Medicaux Intelligents, Laboratoire de neurotechnologies Polystim, Nov. 2014, Nov. 2014, 25 pages.

Wu et al., "Access control schemes for implantable medical devices: A survey", IEEE Internet Things of Journal, vol. 4, No. 5, Oct. 2017, pp. 1272-1283.

European Application No. 20806059.0, "Office Action", Dec. 18, 2024, 7 pages.

* cited by examiner

AUTHORIZING PROGRAMMING OF AN IMPLANTED DEVICE USING SECOND FACTOR

CROSS-REFERENCE TO RELATED APPLICATIONS

This application is a continuation of U.S. patent application Ser. No. 15/930,580 filed May 13, 2020, entitled "AUTHORIZING PROGRAMMING OF AN IMPLANTED DEVICE USING SECOND FACTOR", which claims the benefit of and priority under 35 U.S.C. § 119 to U.S. Provisional Patent Application No. 62/847,359, filed on May 14, 2019, entitled "AUTHORIZING PROGRAMMING OF AN IMPLANTED DEVICE USING SECOND FACTOR," the contents of both of which are hereby incorporated by reference in their entireties for all purposes.

BACKGROUND

A growing number of patients have implantable medical devices to treat or monitor various illnesses. Implantable medical devices may have to pair with an external device, for example, for obtaining information from the implanted device or setting parameters for treatment. In existing systems, security of the implantable medical device is primarily achieved through obscurity. Although communications may be encrypted or otherwise secured, the original pairing connection typically involves no security steps, leaving the patient vulnerable to accidental or malicious manipulation of the implantable medical device.

SUMMARY

Described herein are systems and methods for addressing the lack of security during pairing for a communication connection between an implantable medical device and an external device described above. A system of one or more computers and/or devices can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a system and/or a method for ensuring secure pairing of an external device with an implantable medical device ("IMD"). The IMD may receive a request to pair from an external device (e.g., a clinician's computing device for setting IMD parameters or settings and/or retrieving data from the IMD) over a wireless connection path. In response to receiving the request to pair, the IMD may enable a window of exclusivity for the external device such that other external devices may not pair with the IMD during the window of exclusivity, and the IMD may transmit an authorization instruction message to the external device over the wireless connection path. Such window of exclusivity may prevent other devices from misappropriating the signal to pair, and the direct transmission with authorization instructions may ensure that the external device exclusively receives the instructions. The IMD may, in response to the authorization instruction message, receive, via a second communication path, an authorization pulse from an authorization device (e.g., a charging device of the IMD), where the authorization device is not the external device. The authorization pulse from the charging device may help ensure that the external device is, in fact, authorized to pair with the IMD. For example, the authorization device (e.g., charging device) may require very close proximity to the IMD to send/receive the authorization pulse. Such close proximity helps ensure that the patient is aware of and approves the external device to pair with the IMD. In response to receiving the authorization pulse, finalizing the pairing with the external device. Other embodiments of this aspect include corresponding computer systems, apparatus, and computer programs recorded on one or more computer storage devices, each configured to perform the actions of the methods.

Implementations may include one or more of the following features. In some embodiments, the authorization device is a charging device. In some embodiments, the authorization pulse is an encoded command instructing the IMD to authorize the request to pair. In some embodiments, the request to pair is a request to initiate a pairing relationship between the IMD and the external device using short-wavelength ultra-high frequency radio waves. In some embodiments, the external device is the patient's device (e.g., tablet, smartphone, or the like) or a clinician's device (e.g., tablet, computer, or the like). In some embodiments, engaging the window of exclusivity for the external device includes cancelling a broadcast message. In some embodiments, engaging the window of exclusivity includes declining all other pairing requests. In some embodiments, the authorization instruction message on the external device includes a message requesting the authorization pulse. In some embodiments, the authorization instruction message on the external device includes a message requesting the authorization pulse with the authorization device. In some embodiments, the authorization instruction message includes digital human-comprehensible content describing how a user can cause the authorization device to provide the authorization pulse. In some embodiments, the communication with the external device is secured over the first communication path using an encrypted key pair. In some embodiments, the second communication path is an inductive communication path. In some embodiments the second communication path is a near-field communication path. In some embodiments, the authorization pulse includes metadata uniquely identifying the authorization device. Implementations of the described techniques may include hardware, a method or process, or computer software on a computer-accessible medium.

BRIEF DESCRIPTION OF THE DRAWINGS

A further understanding of the nature and advantages of various examples may be realized by reference to the following figures.

Unless otherwise indicated, elements using the same indicator number are the same elements between differing figures. Some elements may include multiple of the same elements, which are indicated by a letter following the indicator number.

DETAILED DESCRIPTION

An implantable medical device ("IMD") (also referred to herein as implanted device) may communicate with external devices for various reasons. For example, parameters may be set in the IMD or information read out and monitored from the IMD by communication with, for example, the patient's smartphone or a clinician's device such as a tablet or other computing device. It is desirable to ensure that a clinician or patient is connecting to the correct IMD (e.g., not some other nearby IMD) and that unauthorized persons are not connecting to the IMD.

Embodiments described herein include an IMD configured to pair with an external device (e.g., tablet, smartphone, or the like) via, for example, BLUETOOTH® communication. The IMD may receive the pairing request and transmit a request for authorization. The external device may display the request for authorization, prompting the user to provide an authorization pulse. The charging device for the IMD may be configured to send an authorization pulse via the inductive charging coils to the IMD when the charging device is properly aligned with the IMD and, for example, the user presses an authorization button on the charging device. The IMD may receive the authorization pulse and proceed with pairing.

Figure 1:
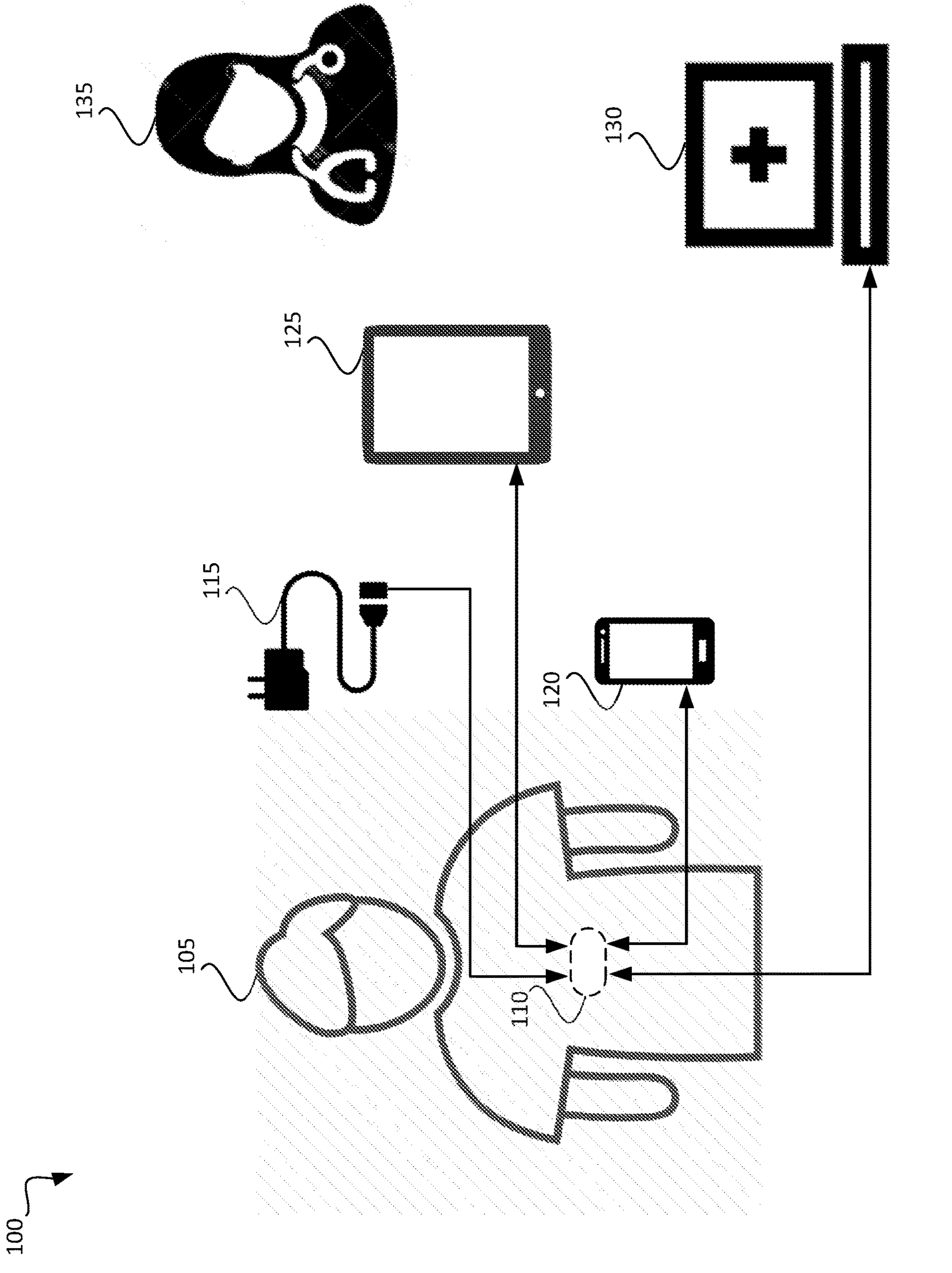
FIG. 1 illustrates a simplified diagram of an implantable medical device system with second factor authorization, according to some embodiments.

FIG. 1 illustrates a simplified diagram 100 of components used for second factor authorization with an IMD 110. The diagram 100 includes the patient 105, the IMD 110, the charging device 115, a patient smartphone 120, a clinician tablet 125, a clinical computing device 130, and a clinician 135.

The IMD 110 may be any implantable medical device such as, for example, an implantable pulse generator ("IPG"), a pacemaker, an implantable cardiac defibrillator, and the like. The IMD 110 may be implanted into the patient 105. The IMD 110 may have at least two interfaces for communicating with external devices. The interfaces may include, for example, a short-range wireless interface, such as, for example, a BLUETOOTH® antenna. Another interface may include an inductive coil, a near-field communication antenna, or any other receiver for receiving mini-range signals. The two interfaces may be different types of interfaces or the same type of interface. Interfaces may include any type of transmission including radio wave communication, magnetic communication using, for example, induction coils, near-field communication, or any other suitable type of communication transmission. Interfaces may use any type of protocol or networking including personal area networks, wide area networks, and the like. Interfaces may further use any suitable technology including ultra-high frequency, short wavelength, infrared, high-speed communication, low-speed communication, low-energy, or any other suitable technology. While patient 105 is shown with a single IMD 110, any number of IMDs may be implanted into patient 105, and the techniques described herein may be used to distinguish between and communicate with each IMD 110 individually.

The charging device 115 may be any suitable device for communicating with the IMD 110. The charging device may include, for example, an inductive coil for generating an electromagnetic field that may be received by the inductive coil in the IMD 110 for charging the IMD 110. To charge the IMD 110, the charging device 115 may be placed close to or touching the body of the patient 105 and aligned with the IMD 110 within the patient 105. The charging device may include a button used to initiate charging of the IMD 110. In some embodiments, the charging device may have an authorization button that initiates an authorization pulse using the inductive coil. For example, the authorization pulse may be a set of short pulses. Any pulsing signal may be used as long as IMD 110 is configured to recognize the pulse pattern as the authorization pulse. The pulses may form an encoded command used by the IMD 110 as an authorization. The authorization pulse contains data, including metadata in some embodiments. As described in more detail herein, the authorization pulse provides data that authorizes and instructs the IMD 110 to complete pairing with the external device (e.g., the patient smartphone 120, clinician tablet 125, clinical computing device 130, or the like). Other messages sent via the charging device 115 to IMD 110 are distinguishable from the authorization pulse. For example, an emergency turn off instruction can be transmitted to the IMD 110 using charging device 115, which is distinguishable from the authorization pulse transmitted using charging device 115.

In some embodiments, rather than a separate authorization button, the button used to initiate charging may be used to transmit the encoded command. For example, a long-hold of the button or a double click may be used to initiate the authorization pulse. Note also that while charging device 115 may be a charging device for charging the IMD 110, any device capable of communicating with the IMD 110 can be used to provide the authorization pulse. Incorporating the authorization pulse capability into the charging device 115 that charges the IMD 110 saves components, cost, and space. However, a separate device can be used to provide the authorization pulse using the inductive coil in the IMD 110 or any other antenna within IMD 110 for receiving the authorization pulse. Further, the method for initiating the authorization pulse may be any suitable component that captures the user or patient intent to send the authorization pulse so that it is unlikely that the user has accidentally triggered the authorization pulse or was tricked into performing the action. For example, long-holding a button or a locked trigger that must be unlocked before triggering would be less likely to be accidentally triggered or a user tricked into triggering. Additionally, use of the charging device that uses an inductive coil for communication is mini-range, such that it is unlikely the patient would be unaware of the authorization pulse action because of the proximity to the patient that is required to transmit an inductive pulse. These various features help ensure the patient actually intends to authorize communication with the external device such as the patient smartphone 120.

Patient smartphone 120 may be any suitable general-purpose electronic device. A general-purpose electronic device is one that performs computing tasks with the ability to store instructions on a memory device and execute those instructions with a processor (e.g., a smartphone, a tablet, a desktop computer, a laptop computer, any mobile computing device, or the like). Patient smartphone 120 may be computing device 400 of FIG. 4, for example. Patient smartphone 120 may be a computing device of the patient 105 used to communicate with the IMD 110. For example, the patient 105 may need to set a parameter of the IMD 110 or monitor a value provided by the IMD 110. Patient smartphone 120 may include at least one compatible interface for communicating with IMD 110. Communication between the IMD 110 and the patient smartphone 120 may be through wireless technology including, for example, short-wavelength radio waves, ultra-high frequency radio waves, a personal area network, a packet-based protocol, a master-slave architecture, any combination thereof, or any other suitable wireless communication technology. For example, patient smartphone 120 may include a short-range (e.g., approximately 35 feet between devices or less) wireless communication interface, such as, for example, a BLUETOOTH® antenna. Patient smartphone 120 may be configured with an interface for obtaining information from or setting parameters of the IMD 110. For example, patient 105 may install an app on patient smartphone 120 that allows the patient 105 to use the patient smartphone 120 to use a graphical user interface to exchange information with the IMD 110. For example, the app may include security certificates used to interface with IMD 110. The patient smartphone 120 may be used via the interface to set parameters on the IMD 110 or obtain information from the IMD 110 (e.g., sensor data). While only one patient smartphone 120 is depicted in FIG. 1, patient 105 may have any number of computing devices that support communication with IMD 110. For example, patient 105 may have a smartphone, a tablet, a notebook computer, a desktop computer, and so forth. Each device may communicate with IMD 110 using the described techniques.

Clinician tablet 125 may be any suitable general-purpose electronic device. Clinician tablet 125 may be computing device 400 of FIG. 4, for example. Clinician tablet 125 may be a computing device used by the clinician 135 used to communicate with IMD 110. For example, the clinician 135 may be performing a service to the patient 105 and, for example, may need to set a parameter of the IMD 110 or monitor a value provided by the IMD 110. Clinician tablet 125 may include at least one compatible interface for communicating with IMD 110. Communication between the IMD 110 and the clinician tablet 125 may be through wireless technology including, for example, short-wavelength radio waves, ultra-high frequency radio waves, a personal area network, a packet-based protocol, a master-slave architecture, any combination thereof, or any other suitable wireless communication technology. For example, clinician tablet 125 may include a short-range wireless communication interface, such as, for example, a BLUETOOTH® antenna. Clinician tablet 125 may be configured with an interface for obtaining information from or setting parameters of the IMD 110. For example, clinician 135 may install an app on clinician tablet 125 that allows the clinician to use the clinician tablet 125 to use a graphical user interface to exchange information with the IMD 110. For example, the app may include security certificates used to interface with IMD 110. The clinician tablet 125 may be used via the interface to set parameters on the IMD 110 or obtain information from the IMD 110 (e.g., sensor data). While only one clinician tablet 125 is depicted in FIG. 1, clinician 135 may have any number of computing devices that support communication with IMD 110. For example, clinician 135 may have a tablet, a smartphone, a notebook computer, a desktop computer, and so forth. Each device may communicate with IMD 110 using the described techniques.

Clinical computing device 130 may be any suitable general-purpose electronic device. Clinical computing device 130 may be computing device 400 of FIG. 4, for example. Hospitals and other medical facilities may have any number of clinical computing devices 130 that may be used to interface with IMD 110. Clinical computing device 130 may be a computing device used by the clinician 135 that may be performing a service to the patient 105, and the clinician 135 may use the clinical computing device 130 to communicate with IMD 110. For example, the clinician 135 may need to set a parameter of the IMD 110 or monitor a value provided by the IMD 110. Clinical computing device 130 may include at least one compatible interface for communicating with IMD 110. Communication between the IMD 110 and the clinical computing device 130 may be through wireless technology including, for example, short-wavelength radio waves, ultra-high frequency radio waves, a personal area network, a packet-based protocol, a master-slave architecture, any combination thereof, or any other suitable wireless communication technology. For example, clinical computing device 130 may include a short-range wireless communication interface, such as a BLUETOOTH® antenna. Clinical computing device 130 may be configured with an interface for obtaining information from or setting parameters of the IMD 110. For example, clinician 135 may install an app on clinical computing device 130 that allows the clinician to use the clinical computing device 130 to use a graphical user interface to exchange information with the IMD 110. For example, the app may include security certificates used to interface with IMD 110. The clinical computing device 130 may be used via the interface to set parameters on the IMD 110 or obtain information from the IMD 110 (e.g., sensor data). While only one clinical computing device 130 is depicted in FIG. 1, clinician 135 may have any number of computing devices that support communication with IMD 110. Each device may communicate with IMD 110 using the described techniques.

Figure 2:
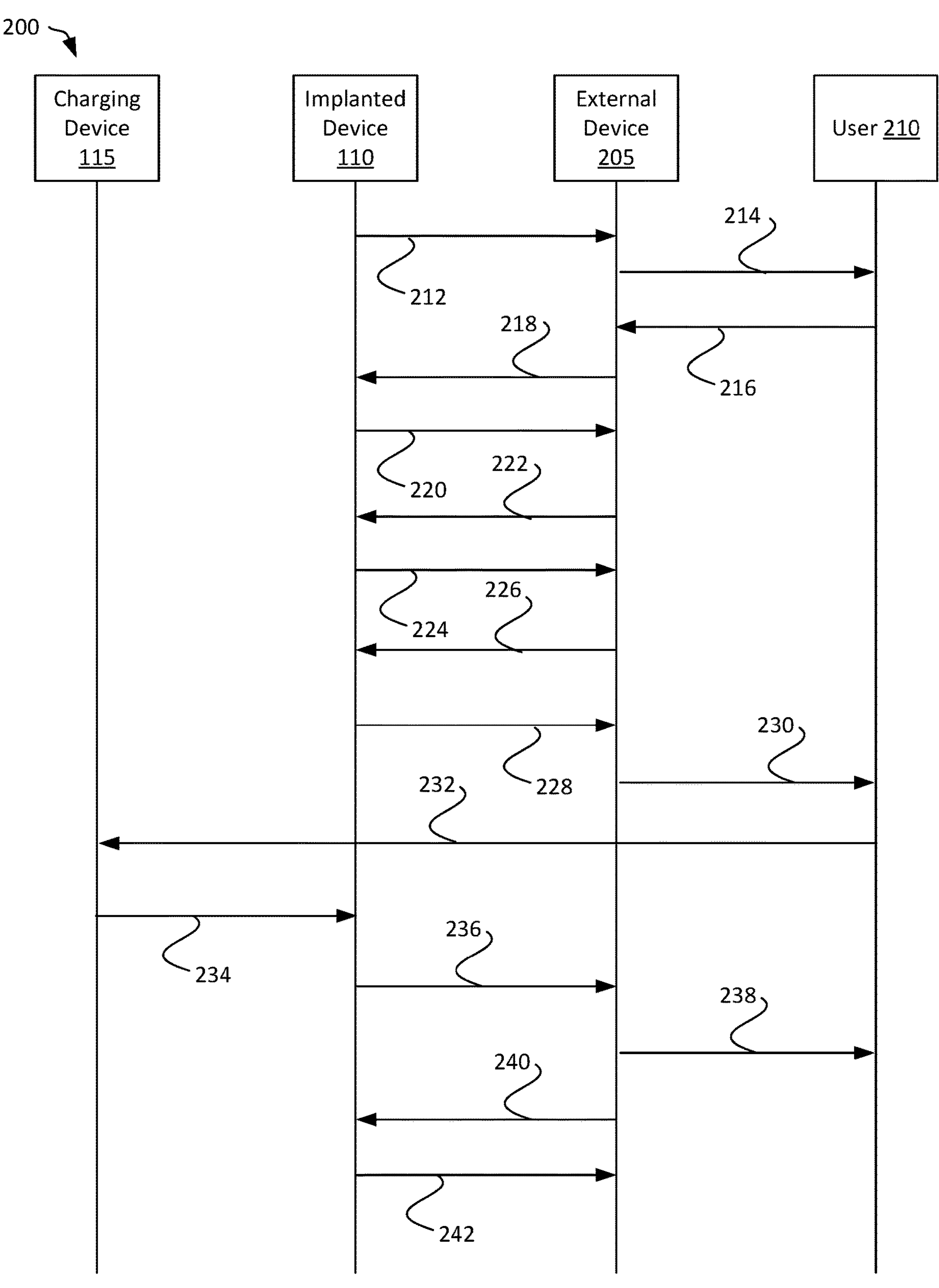
FIG. 2 illustrates a swim diagram of communication exchanges for pairing an implantable medical device with an external device.

FIG. 2 illustrates a swim diagram 200 showing message passing during pairing. Along the top of the swim diagram 200 are the components used at each stage including the charging device 115, implanted device 110, external device 205, and user 210. External device 205 may be any of patient smartphone 120, clinician tablet 125, or clinical computing device 130. User 210 may be any of patient 105 and clinician 135. In some embodiments, another authorization device may be used other than the charging device 115, in which case the charging device 115 may be replaced in the swim diagram 200 with another authorization device.

At communication arrow 212, the IMD 110 may advertise its presence using, for example, a broadcast message over, for example a short-range wireless communication network (e.g., BLUETOOTH®). External device 205 may receive the advertisement and provide a user interface ("UI") prompt to the user 210. For example, the user 210 may open the installed app and look for available devices. The advertisement from IMD 110 may prompt the UI to update showing the IMD 110 as available for connection.

The user 210 may select IMD 110 from the UI, and the selection may be received at the external device 205 at communication arrow 216. At communication arrow 218 the external device 205 may initiate a communication channel with IMD 110 (e.g., BLUETOOTH® low energy bond). At communication arrow 220 IMD 110 may complete the communication channel with a response. The short-range wireless communication channel (e.g., BLUETOOTH®) may be insecure at this point.

At communication arrow 222, external device 205 may transmit a list of supported protocol version numbers as well as a public key. The public key may be generated from the app installed on external device 205. At communication arrow 224, IMD 110 may transmit a response to external device 205 that includes, for example, the protocol version number, an IMD certificate, an indication of whether the external device 205 is pre-authorized, and a pseudorandom value that is, for example, 32 bytes. Upon receipt of the response, external device 205 may verify the IMD certificate by checking that the IMD certificate chains back to the common trust root using, for example, the X.509-based public key infrastructure.

At communication arrow 226, the external device 205 transmits back to the IMD 110 an external device certificate and the 32 byte pseudorandom value. Upon receipt, IMD 110 may verify the external device certificate. If the external device public key is saved as trusted, then pairing is complete and no further steps are necessary. Otherwise, the IMD 110 checks that the external device certificate chains back to the common trust root using, for example, the X.509-based public key infrastructure.

At communication arrow 228 the IMD 110 sends a request for authorization to the external device 205. The external device generates a UI prompt and displays it to the user 210 as shown by communication arrow 230. The UI prompt may be a prompt that is displayed in the app that is textual and/or may include an image. For example, the UI prompt may be text that states "Provide authorization" or the like. As another example, an image of the charger (or other authorization device if the charging device 115 is not used for the authorization device) being aligned with the IMD 110 may be shown. The image may be animated, for example.

At communication arrow 232, the user 210 may access the charging device 115. The user may align the charging device 115 with the IMD 110 as if the user were going to charge the IMD. Rather than initiating charging, the user 210 may initiate an authorization pulse. For example, the user 210 may long-press a button on the charging device 115 to initiate the authorization pulse. If the charging device 115 is properly aligned with the IMD 110, the IMD 110 may receive the authorization pulse as shown by communication arrow 234. The authorization pulse may be, for example, a pulsed signal over inductive charging coils. The charging device 115 that provides the authorization pulse may provide the same authorization pulse to any IMD 110. In some embodiments, the charging device 115 may be uniquely coupled to the IMD 110 such that a unique authorization pulse is provided to IMD 110 that would not work for other IMDs. The pulsed signal may be, for example, transmission of data through patterns of an on/off signal (i.e., a digital signal). Any suitable pulsing pattern may be used as long as IMD 110 is configured to recognize the pulsing pattern. For example, IMD 110 may be configured to recognize a specific pulsing pattern as an authorization pulse in response to a request for authorization. When IMD 110 is awaiting an authorization pulse and receives the current pulsing pattern, IMD 110 will recognize the authorization pulse and proceed with pairing. The data contained in the pulsed signal may include additional data (e.g., metadata) that may be unique to a specific IMD 110 and/or charging device 115. The charging device 115 may be uniquely coupled to the IMD 110, and the metadata may be used to confirm the correct charging device 115 is communicating with the correct IMD 110, for example. The authorization pulse provides data that authorizes and instructs the IMD 110 to complete pairing with the external device (e.g., the patient smartphone 120, clinician tablet 125, clinical computing device 130, or the like). Other messages sent via the charging device 115 to IMD 110 are distinguishable from the authorization pulse. For example, an emergency turn off instruction can be transmitted to the IMD 110 using charging device 115, which is distinguishable from the authorization pulse transmitted using charging device 115.

Upon receiving the authorization pulse, IMD 110 may save the external device certificate and compute the session key to finalize pairing with the external device 205. At communication arrow 236, the IMD 110 may send an indication that pairing is complete to external device 205. Future communications may use the generated session key. The session key may be used to ensure application data exchanged between the IMD 110 and external device 205 is encrypted. At communication arrow 238, external device 205 may provide an indication to user 210 that pairing is successful via a message displayed to the user 210. In some embodiments, if the authorization pulse is not received within a threshold period of time, the authorization period may time out, and the process may have to begin again at communication arrow 212.

At communication arrows 240 and 242, external device 205 and IMD 110 may exchange application data using the session key. For example, the IMD 110 may provide data to the external device 205 including configuration setting information and sensor collection data, for example. The external device 205 may request such data and, for example, modify configuration setting information in the IMD 110.

Figure 3:
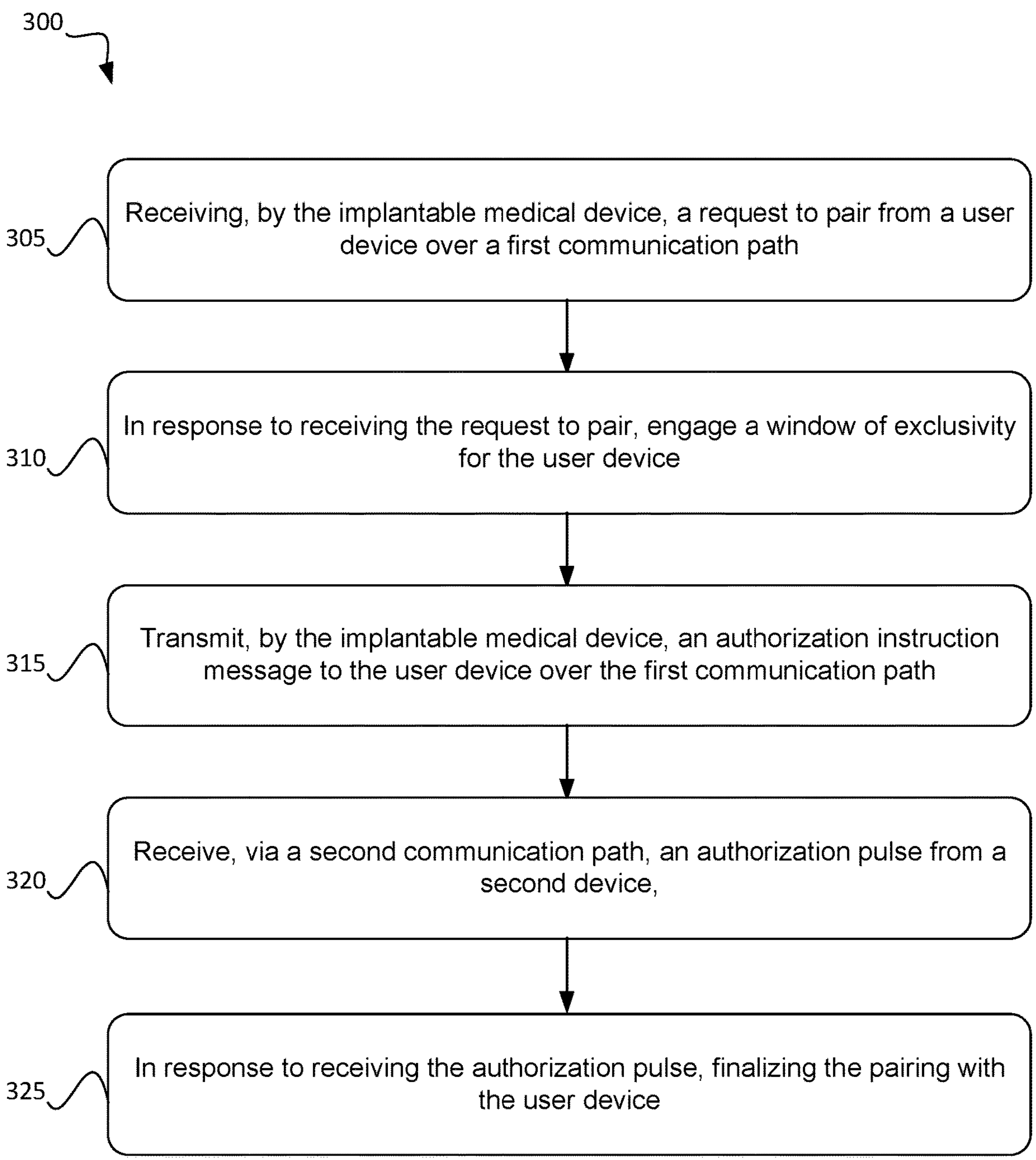
FIG. 3 illustrates a method of implementing second factor authorization for an implantable medical device according to some embodiments.

FIG. 3 illustrates a method 300 for using second factor authorization between an IMD and an external device. Method 300 may be performed by, for example, an IMD, such as IMD 110. Method 300 begins with step 305 when the IMD receives a request to pair from a user device over a first communication path. The first communication path may use a first communication protocol. The first communication path may use a first communication interface of the IMD to send and receive signals to communicate with a communication interface of the external device. For example, the user device may be a patient device (e.g., patient smartphone 120) or a clinician device (e.g., clinician tablet 125 or clinical computer system 130) having a communication interface that may be used to communicate with the first communication interface of the IMD. The request to pair may come in response to an advertisement or broadcast sent by the IMD for communication using the first communication interface. The first communication path may be a short range wireless communication path such as, for example, BLUETOOTH®. The pairing request may be, for example, a BLUETOOTH® pairing request.

At step 310, in response to receiving the request to pair, the IMD may engage a window of exclusivity for the user device. The window of exclusivity may be a specific time window during which no device other than the user device that sent the request to pair to the IMD may pair with the IMD. For example, any requests to pair that the IMD receives during the window of exclusivity may be denied. In some embodiments, the IMD may stop broadcasting or advertising its presence during the window of exclusivity. The window of exclusivity may be any amount of time sufficient for a user to provide the authorization pulse such as, for example, any amount of time between thirty (30) seconds to one hundred twenty (120) seconds, though the window may be shorter than thirty seconds or longer than one hundred twenty seconds. This window of exclusivity may prevent other devices from intruding or sniping the authorization. If the window of exclusivity ends without authorization, the pairing request may be denied. If the pairing completes successfully, the window of exclusivity can be terminated in some embodiments. Once the window of exclusivity ends, the IMD may pair with other devices again. A new request to pair may then initiate to cause the IMD to engage a new window of exclusivity for the device that sent the new request to pair.

At step 315, the IMD may transmit an authorization instruction message to the user device over the first communication path. The authorization instruction message may be an indication to provide the authorization pulse. The authorization instruction message may contain digital human-comprehensible content that describes how the user may provide the authorization pulse and may include text, images, video, audio, or any combination thereof. The authorization instruction message may contain an instruction for the user device to display a message on a graphical user interface to the user to provide the authorization pulse. In some embodiments, the instruction to display the message may indicate that the user should provide the authorization pulse with the authorization device and/or may include the message to display including text, images, video, and audio. The user device may provide a prompt to the user to provide the authorization pulse. For example, the prompt may include a textual, graphical, or animated indication, such as an image of aligning the charging device with the IMD and an arrow pointing to the authorization button, to prompt the user to send the authorization pulse. Receiving this indication from the IMD may help the user know that he or she is connecting to the correct IMD. The authorization pulse may be provided by the user by, for example, aligning the charging device for the IMD with the IMD as though the user were going to initiate charging. Then, rather than initiating charging, the user may, for example, press a special authorization button or, as another example, long press the charge initiation button to initiate the authorization pulse. The authorization pulse may be a set of short pulses sent through the charging induction coils of the charging device to the charging induction coils of the IMD. The authorization pulse may include an indication that it is the authorization pulse. In some embodiments, engaging the window of exclusivity may cause the IMD to accept any pulse received over the second communication path, by a charging device, and/or by the expected receiving antenna or component as the authorization pulse. Induction communication is very close range (i.e., mini-range) (e.g., less than one (1) foot), meaning the authorization pulse may not be sent and received by the IMD without the patient likely being aware because the charging device must be, in many cases, touching the patient or within an inch at most. With, for example, a charging device, a user will typically hold the charging device against the body with only body tissue and clothing between the charging device and the IMD. Other communications can be used, such as near-field communication for transmitting the authorization pulse. However, to ensure security, the communication may be mini-range for the authorization communication protocol. Further, additional antennas increase the size of the IMD, which is ideally as small as possible since it is implanted in the patient. Since the IMD will already have induction coils and communicate with the charging device to charge the IMD, using the charging device to send the authorization pulse removes the need to increase the size of the IMD to accommodate an additional antenna.

At step 320, the IMD receives the authorization pulse from the second device (e.g., charging device) over a second communication path. The second communication path may use a different protocol than the protocol used for the first communication path, or the second communication path may use the same protocol than the protocol used for the first communication path. The second communication path may use a second communication interface of the IMD. For example, the second communication interface may be an induction coil while the first communication interface may be a radio wave transceiver. At step 325, in response finalizes the pairing with the user device. When the pairing is finalized, the user can be assured that he or she paired with the correct IMD since the authorization pulse was sent to the specific IMD. Upon finalizing pairing, the user device can communicate with the IMD over the first communication path such that general purpose components of the user device can now send messages across the communication path. For example, a configuration application on the user device may be used to transmit parameter values (e.g., configuration settings) to the IMD over the first communication path to set the parameter values within the IMD. When the IMD receives the parameter values over the first communication path, the IMD may modify the parameter values stored within the IMD to those sent from the user device.

Figure 4:
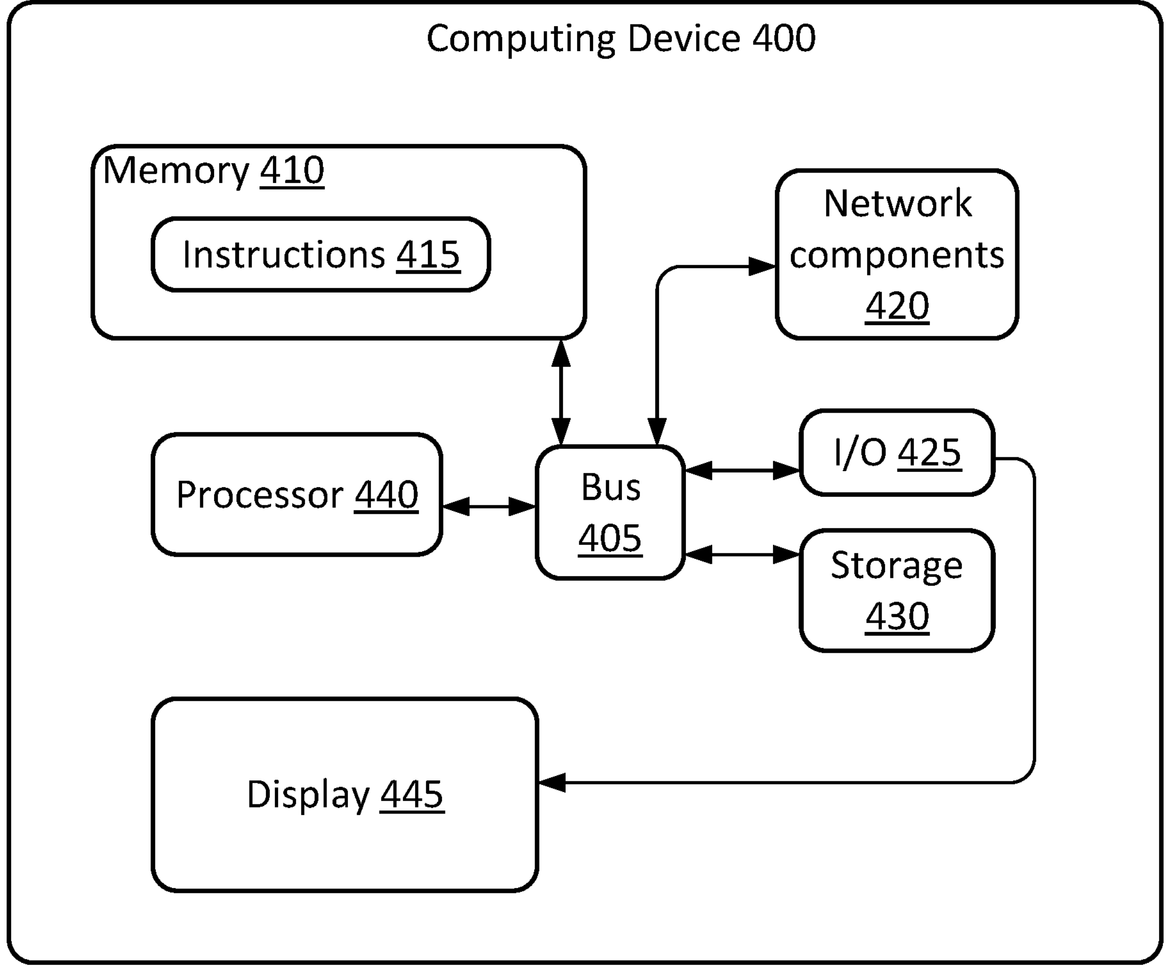
FIG. 4 illustrates an exemplary computer system.

FIG. 4 illustrates a block diagram of an example computer system 400. Computer system 400 can be any of the described computers herein including, for example, smartphone 120, tablet 125, or machine 130. The computing device 400 can be or include, for example, a laptop computer, desktop computer, tablet, e-reader, smart phone or mobile device, smart watch, personal data assistant (PDA), or other electronic device.

The computing device 400 can include a processor 440 interfaced with other hardware via a bus 405. A memory 410, which can include any suitable tangible (and non-transitory) computer readable medium, such as RAM, ROM, EEPROM, or the like, can embody program components (e.g., instructions 415) that configure operation of the computing device 400. In some examples, the computing device 400 can include input/output ("I/O") interface components 425 (e.g., for interfacing with a display 445, keyboard, or mouse) and additional storage 430.

The computing device 400 can include network components 420. Network components 420 can represent one or more of any components that facilitate a network connection. In some examples, the network components 420 can facilitate a wireless connection and include wireless interfaces such as IEEE 802.11, BLUETOOTH®, or radio interfaces for accessing cellular telephone networks (e.g., a transceiver/antenna for accessing CDMA, GSM, UMTS, or other mobile communications network). In other examples, the network components 420 can be wired and can include interfaces such as Ethernet, USB, or IEEE 1394.

Although FIG. 4 depicts a single computing device 400 with a single processor 440, the system can include any number of computing devices 400 and any number of processors 440. For example, multiple computing devices 400 or multiple processors 440 can be distributed over a wired or wireless network (e.g., a Wide Area Network, Local Area Network, or the Internet). The multiple computing devices 400 or multiple processors 440 can perform any of the steps of the present disclosure individually or in coordination with one another.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

Different arrangements of the components depicted in the drawings or described above, as well as components and steps not shown or described are possible. Similarly, some features and sub-combinations are useful and may be employed without reference to other features and sub-combinations. Embodiments of the present disclosure have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the present disclosure, a single component may be replaced by multiple components, and multiple components may be replaced by a single component, to provide an element or structure or to perform a given function or functions. Except where such substitution would not be operative to practice certain embodiments of the present disclosure, such substitution is considered within the scope of the present disclosure.

It is to be understood that the figures and descriptions of embodiments of the present disclosure have been simplified to illustrate elements that are relevant for a clear understanding of the present disclosure. Those of ordinary skill in the art will recognize, however, that these and other elements may be desirable. However, because such elements are well known in the art, and because they do not facilitate a better understanding of the present disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the present disclosure, a single component may be replaced by multiple components, and multiple components may be replaced by a single component, to provide an element or structure or to perform a given function or functions. Except where such substitution would not be operative to practice certain embodiments of the present disclosure, such substitution is considered within the scope of the present disclosure. A recitation of "a", "an" or "the" is intended to mean "one or more" unless specifically indicated to the contrary.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

The examples presented herein are intended to illustrate potential and specific implementations of the present disclosure. It can be appreciated that the examples are intended primarily for purposes of illustration of the present disclosure for those skilled in the art. There may be variations to these diagrams or the operations described herein without departing from the spirit of the present disclosure. For instance, in certain cases, method steps or operations may be performed or executed in differing order, or operations may be added, deleted or modified.

Furthermore, whereas particular embodiments of the present disclosure have been described herein for the purpose of illustrating the present disclosure and not for the purpose of limiting the same, it will be appreciated by those of ordinary skill in the art that numerous variations of the details, materials and arrangement of elements, steps, structures, and/or parts may be made within the principle and scope of the present disclosure without departing from the present disclosure as described in the claims.

What is claimed is:

1. A method, comprising:

receiving, by a medical device, a request to pair from an external device over a first wireless communication path;

in response to receiving the request to pair:

enabling, by the medical device, a window of exclusivity for pairing with the external device, and transmitting, by the medical device, an authorization instruction message to the external device over the first wireless communication path;

during the window of exclusivity, receiving, by the medical device from the external device via a second wireless communication path, an authorization pulse; and in response to receiving the authorization pulse by the medical device, pairing with the external device.

2. The method of claim 1, wherein the authorization pulse is received from an authorization device.

3. The method of claim 2, wherein the authorization device is a charging device for the medical device.

4. The method of claim 2, wherein the authorization pulse is an encoded command instructing the medical device to authorize the request to pair.

5. The method of claim 2, wherein the authorization device is not the external device.

6. The method of claim 1, wherein the request to pair is a request to initiate a pairing relationship between the medical device and the external device using short-wavelength ultra-high frequency radio waves.

7. The method of claim 1, wherein engaging the window of exclusivity comprises declining all other pairing requests over a communication protocol of the first wireless communication path while the window of exclusivity is active.

8. The method of claim 1, wherein the medical device is implanted into a patient, and wherein the external device is configured with an interface for obtaining information from or setting parameters of the medical device.

9. The method of claim 1, wherein the second wireless communication path is an inductive communication path or a near-field communication path.

10. The method of claim 1, further comprising:

broadcasting an advertisement packet; and stop broadcasting the advertisement packet during the window of exclusivity.

11. A medical device comprising:

a first antenna;

a second antenna;

a processor; and a non-transitory computer-readable medium storing instructions that, when executed by the processor, cause the processor to:

receive a request to pair from an external device over a first wireless communication path via the first antenna;

in response to receiving the request to pair:

enable, by the medical device, a window of exclusivity for pairing with the external device, and transmit, by the medical device, an authorization instruction message to the external device over the first wireless communication path;

during the window of exclusivity, receive, by the medical device from the external device via a second wireless communication path via the second antenna, an authorization pulse; and in response to receiving the authorization pulse by the medical device, pairing with the external device.

12. The medical device of claim 11, wherein the authorization pulse is received from an authorization device.

13. The medical device of claim 12, wherein the authorization device is a charging device for the medical device.

14. The medical device of claim 12, wherein the authorization pulse is an encoded command instructing the medical device to authorize the request to pair.

15. The medical device of claim 12, wherein the authorization device is not the external device.

16. The medical device of claim 11, wherein the request to pair is a request to initiate a pairing relationship between the medical device and the external device using short-wavelength ultra-high frequency radio waves.

17. The medical device of claim 11, wherein engaging the window of exclusivity comprises declining all other pairing requests over a communication protocol of the first wireless communication path while the window of exclusivity is active.

18. The medical device of claim 11, wherein the medical device is implanted into a patient, and wherein the external device is configured with an interface for obtaining information from or setting parameters of the medical device.

19. The medical device of claim 11, wherein the second wireless communication path is an inductive communication path or a near-field communication path.

20. The medical device of claim 11, wherein the non-transitory computer-readable medium further stores instructions that, when executed by the processor, cause the processor to:

broadcast an advertisement packet; and stop broadcast of the advertisement packet during the window of exclusivity.

* * * * *